US010473528B2

(12) United States Patent
Sakami et al.

(10) Patent No.: US 10,473,528 B2
(45) Date of Patent: Nov. 12, 2019

(54) OPTICAL APPARATUS AND SIGHT TUBE FOR INSPECTING TURBINE ENGINE COMPONENTS

(71) Applicant: General Electric Company, Schenectady, NY (US)

(72) Inventors: Mohamed Sakami, West Chester, OH (US); Nirm Velumylum Nirmalan, Liberty Township, OH (US); Jeremy Clyde Bailey, Liberty Township, OH (US)

(73) Assignee: General Electric Company, Schenectady, NY (US)

( * ) Notice: Subject to any disclaimer, the term of this patent is extended or adjusted under 35 U.S.C. 154(b) by 307 days.

(21) Appl. No.: 15/043,508

(22) Filed: Feb. 13, 2016

(65) Prior Publication Data

US 2017/0234734 A1    Aug. 17, 2017

(51) Int. Cl.
*G01J 5/06* (2006.01)
*G01J 5/00* (2006.01)
(Continued)

(52) U.S. Cl.
CPC .......... *G01J 5/061* (2013.01); *F02D 41/1451* (2013.01); *G01J 5/0088* (2013.01); *G01N 21/954* (2013.01); *G02B 7/028* (2013.01); *G02B 23/243* (2013.01); *G02B 23/2492* (2013.01); *H04N 5/2254* (2013.01); *G01J 2005/0077* (2013.01); *G01M 15/14* (2013.01);
(Continued)

(58) Field of Classification Search
CPC ...... G01J 5/029; G01J 5/061; G02B 23/2492; G02B 7/028

USPC ....... 73/112.01–112.06; 415/118; 356/43–50
See application file for complete search history.

(56) References Cited

U.S. PATENT DOCUMENTS 4,815,276 A    3/1989   Hansel et al.
5,120,252 A    6/1992   Mayo et al.
(Continued)

FOREIGN PATENT DOCUMENTS

CN    102576148 A    7/2012
CN    102589003 A    7/2012
(Continued)

OTHER PUBLICATIONS

Extended European Search Report and Opinion issued in connection with corresponding EP Application No. 17155204.5 dated Jun. 22, 2017.
(Continued)

*Primary Examiner* — Zachary W Wilkes
(74) *Attorney, Agent, or Firm* — McGarry Bair, P.C.

(57) ABSTRACT

An apparatus for insertion through an opening in an outer casing of a gas turbine engine and inspection of internal turbine components at elevated temperatures having an optical sight tube configured to optically communicate with an interior of gas turbine engine via a distal end disposed at the interior and a proximal end disposed exterior of the internal turbine components and defined by a first longitudinal wall, at least one lens at the distal end of the optical sight tube adjacent to the longitudinal wall; and at least one longitudinal cooling groove in the longitudinal wall for flowing a cooling medium from a location external to the turbine to cool the optical sight tube at a location at least adjacent the distal end.

16 Claims, 8 Drawing Sheets

(51) Int. Cl.
   *G02B 23/24* (2006.01)
   *G02B 7/02* (2006.01)
   *F02D 41/14* (2006.01)
   *G01N 21/954* (2006.01)
   *H04N 5/225* (2006.01)
   *G01N 25/72* (2006.01)
   *G01M 15/14* (2006.01)
   *G01N 21/15* (2006.01)

(52) U.S. Cl.
   CPC ....... *G01N 25/72* (2013.01); *G01N 2021/151* (2013.01); *G01N 2021/9542* (2013.01); *H04N 2005/2255* (2013.01)

(56) References Cited

U.S. PATENT DOCUMENTS

| | | | |
|---|---|---|---|
| 5,146,244 A * | 9/1992 | Myhre | B08B 17/02 356/43 |
| 7,121,098 B2 | 10/2006 | Hatcher | |
| 7,662,091 B2 | 2/2010 | Bagley et al. | |
| 8,184,151 B2 | 5/2012 | Zombo et al. | |
| 8,439,630 B2 | 5/2013 | Lemieux et al. | |
| 8,674,257 B2 * | 3/2014 | Li | B23K 26/0648 219/121.65 |
| 8,727,706 B2 | 5/2014 | DeLancey et al. | |
| 9,015,002 B2 | 4/2015 | Zombo et al. | |
| 9,435,750 B2 * | 9/2016 | Matsumoto | G02B 23/2484 |
| 2005/0281520 A1 | 12/2005 | Kehoskie et al. | |
| 2007/0107504 A1 | 5/2007 | Smed et al. | |
| 2008/0242927 A1 | 10/2008 | Hirata | |
| 2009/0259103 A1 | 10/2009 | Hirata | |
| 2012/0171015 A1 | 7/2012 | DeLancey et al. | |
| 2012/0174590 A1 * | 7/2012 | Krull | F23N 5/082 60/772 |

FOREIGN PATENT DOCUMENTS

| | | | | |
|---|---|---|---|---|
| DE | 3017144 A1 | 11/1981 | | |
| EP | 2 888 577 A1 | 7/2015 | | |
| GB | 865140 A * | 4/1961 | ............. | G01J 5/029 |
| WO | 2011152906 A2 | 12/2011 | | |

OTHER PUBLICATIONS

Machine translation and First Office Action issued in connection with corresponding CN Application No. 201710076037.6 dated Jan. 25, 2019.

* cited by examiner

OPTICAL APPARATUS AND SIGHT TUBE FOR INSPECTING TURBINE ENGINE COMPONENTS

BACKGROUND OF THE INVENTION

Turbine engines, and particularly gas or combustion turbine engines, are rotary engines that extract energy from a flow of combusted gases passing through the engine onto a multitude of turbine blades. Gas turbine engines have been used for land and nautical locomotion and power generation, but are most commonly used for aeronautical applications such as for aircraft, including helicopters. In aircraft, gas turbine engines are used for propulsion of the aircraft. In terrestrial applications, turbine engines are often used for power generation.

Gas turbine engines for aircraft are designed to operate at high temperatures to maximize engine efficiency. Temperatures in the high pressure turbine are around 1000° C. to 2000° C. and fluid from the compressor is around 500° C. to 760° C. Internal components of gas and steam turbines, for example, steam turbine blades are typically visually inspected, during a turbine outage, by inserting a borescope through an opening in the outer turbine shell and articulating the video head of the borescope to achieve the desired inspection view. Typically a waiting period is necessary after shutdown and before inspection because current borescope inspection equipment has a temperature limit of approximately 50° C. As a result of this temperature limitation, gas and steam turbine inspections cannot be performed until the turbine cools down from its normal operating temperature.

BRIEF DESCRIPTION OF THE INVENTION

In one aspect, the invention relates to an apparatus for insertion through an opening in an outer casing of a turbine engine and inspection of internal turbine components at elevated temperatures including a hollow optical sight tube configured to optically communicate with an interior of a gas turbine engine via a distal end disposed at the interior of the gas turbine engine and a proximal end disposed exterior of the internal turbine components and defined by a first longitudinal wall defining a continuous, even, and concentric interior surface, and at least two lenses received within the hollow optical sight tube, the at least two lenses fixed to a first portion of the interior surface of the first longitudinal wall at the distal end of the optical sight tube, and not fully contacting a second portion of the longitudinal wall, wherein a space between the second portion and the at least two lenses defines a longitudinal lens cooling groove of each of the at least two lenses, and wherein the cooling groove of each of the at least two lenses are axially aligned along the first longitudinal wall, the lens cooling groove arranged for flowing a cooling medium from a location external to the turbine to cool the hollow optical sight tube at a location at least adjacent the distal end.

In another aspect, the invention relates to an optical sight tube for viewing internal components of a turbine engine, including a first elongated wall defining a continuous, even, and concentric interior surface, and at least two lenses proximate to an interior distal end of the first elongated wall, each of the at least two lenses fixed at a relative first portion of the interior surface of the first elongated wall and not fully contacting a relative second portion of the interior surface of the first elongated wall, wherein a space between the second portion and the at least two lenses defines a lens cooling groove of each of the at least two lenses, and wherein the cooling groove of each of the at least two lenses are axially aligned along the first elongated wall such that the lens cooling groove is configured for flowing a cooling medium from a location external to the turbine to cool the optical sight tube at a location at least adjacent the distal end.

DESCRIPTION OF EMBODIMENTS OF THE INVENTION

The various aspects described herein relate to an optical imaging system with an optical sight tube such as a borescope assembly and method for inspecting internal components of a turbine engine while the turbine engine is being operated. Installing optics to monitor and image hot gas path components such as airfoils and combustors, in an operating gas turbine is not a relatively easy or straight-forward task. Presently, rigid optics transmit light with higher imaging fidelity than fiber optics and thus rigid optics can be located inside a gas turbine to relay images to a convenient location where an imaging device such as an infrared (IR) camera can be placed. However, to image its interior with a fixed optics probe, an engine has to be shut down. The various aspects described herein relate to an optical imaging system with an optical sight tube such that, while a gas turbine is operating, different regions of the hot gas path can be viewed by remotely moving the probe. The various aspects described herein improve the efficiency in testing and allow more regions to be viewed. Further, the various aspects described herein can be particularly useful in viewing a shroud above a set of rotating turbine blades in a gas turbine engine.

Figure 1:
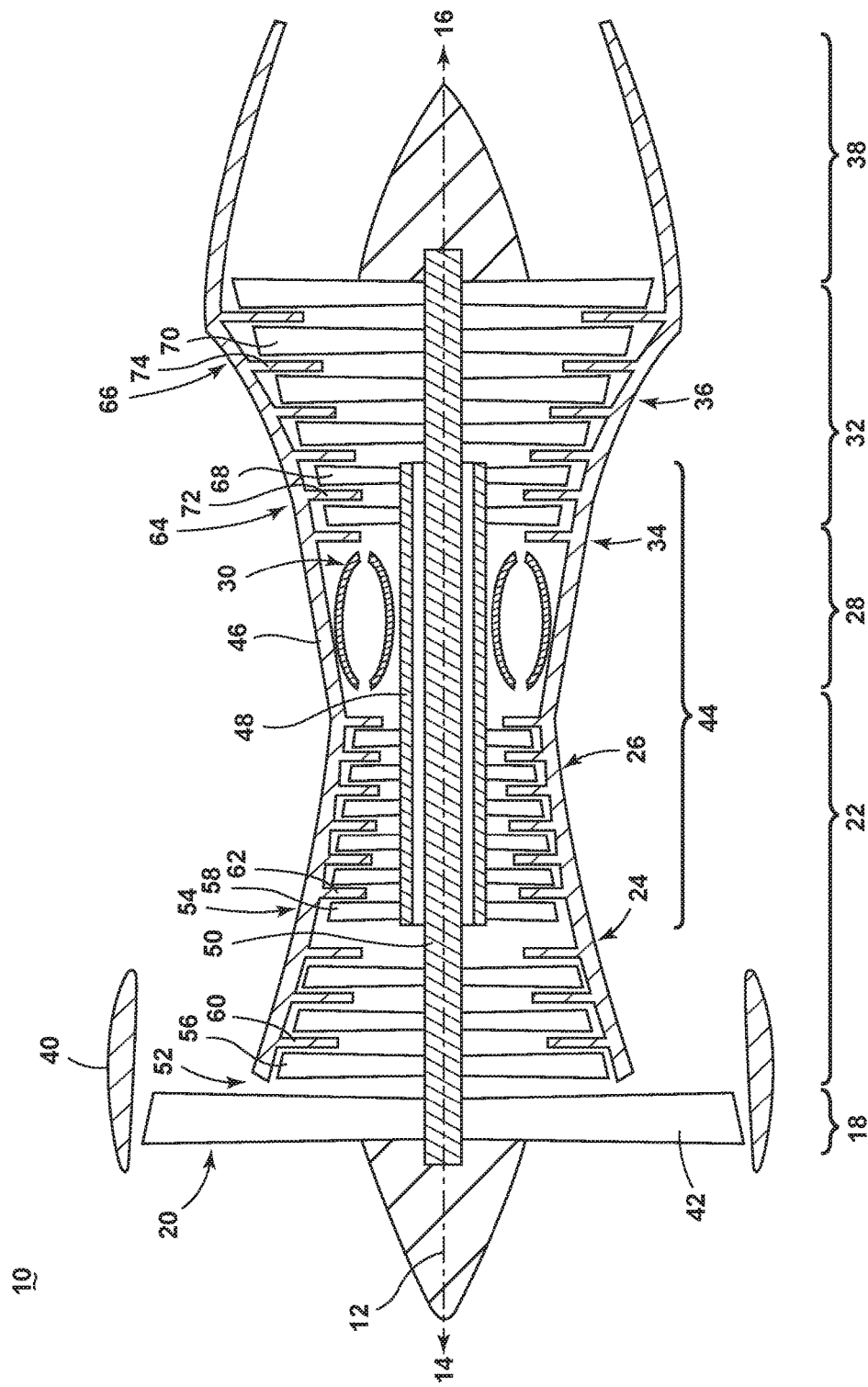
FIG. 1 is a schematic cross-sectional diagram of a gas turbine engine for an aircraft.

For purposes of illustration, the present invention will be described with respect to an aircraft gas turbine engine. It will be understood, however, that the invention is not so limited and may have general applicability in non-aircraft applications, such as other mobile applications and non-mobile industrial, commercial, and residential applications. FIG. 1 is a schematic cross-sectional diagram of a conventional gas turbine engine 10 for an aircraft in which an optical imaging system described herein can operate. The engine 10 has a generally longitudinally extending axis or centerline 12 extending forward 14 to aft 16. The engine 10 includes, in downstream serial flow relationship, a fan section 18 including a fan 20, a compressor section 22 including a booster or low pressure (LP) compressor 24 and a high pressure (HP) compressor 26, a combustion section 28 including a combustor 30, a turbine section 32 including a HP turbine 34 and a LP turbine 36, and an exhaust section 38.

The fan section 18 includes a fan casing 40 surrounding the fan 20. The fan 20 includes a plurality of fan blades 42 disposed radially about the centerline 12.

The HP compressor 26, the combustor 30, and the HP turbine 34 form a core 44 of the engine 10 which generates combustion gases. The core 44 is surrounded by core casing 46 which can be coupled with the fan casing 40.

A HP shaft or spool 48 disposed coaxially about the centerline 12 of the engine 10 drivingly connects the HP turbine 34 to the HP compressor 26. A LP shaft or spool 50, which is disposed coaxially about the centerline 12 of the engine 10 within the larger diameter annular HP spool 48, drivingly connects the LP turbine 36 to the LP compressor 24 and fan 20.

The LP compressor 24 and the HP compressor 26 respectively include a plurality of compressor stages 52, 54, in which a set of compressor blades 56, 58 rotate relative to a corresponding set of static compressor vanes 60, 62 (also called a nozzle) to compress or pressurize the stream of fluid passing through the stage. In a single compressor stage 52, 54, multiple compressor blades 56, 58 can be provided in a ring and extend radially outwardly relative to the centerline 12, from a blade platform to a blade tip, while the corresponding static compressor vanes 60, 62 are positioned downstream of and adjacent to the rotating blades 56, 58. It is noted that the number of blades, vanes, and compressor stages shown in FIG. 1 were selected for illustrative purposes only, and that other numbers are possible.

The HP turbine 34 and the LP turbine 36 respectively include a plurality of turbine stages 64, 66, in which a set of turbine blades 68, 70 are rotated relative to a corresponding set of static turbine vanes 72, 74 (also called a nozzle) to extract energy from the stream of fluid passing through the stage. In a single turbine stage 64, 66, multiple turbine blades 68, 70 can be provided in a ring and extend radially outwardly relative to the centerline 12, from a blade platform to a blade tip, while the corresponding static turbine vanes 72, 74 are positioned upstream of and adjacent to the rotating blades 68, 70. It is noted that the number of blades, vanes, and turbine stages shown in FIG. 1 were selected for illustrative purposes only, and that other numbers are possible.

In operation, the rotating fan 20 supplies ambient air to the LP compressor 24, which then supplies pressurized ambient air to the HP compressor 26, which further pressurizes the ambient air. The pressurized air from the HP compressor 26 is mixed with fuel in the combustor 30 and ignited, thereby generating combustion gases. Some work is extracted from these gases by the HP turbine 34, which drives the HP compressor 26. The combustion gases are discharged into the LP turbine 36, which extracts additional work to drive the LP compressor 24, and the exhaust gas is ultimately discharged from the engine 10 via the exhaust section 38. The driving of the LP turbine 36 drives the LP spool 50 to rotate the fan 20 and the LP compressor 24.

Some of the ambient air supplied by the fan 20 can bypass the engine core 44 and be used for cooling of portions, especially hot portions, of the engine 10, and/or used to cool or power other aspects of the aircraft. In the context of a turbine engine, the hot portions of the engine are normally downstream of the combustor 30, especially the turbine section 32, with the HP turbine 34 being the hottest portion as it is directly downstream of the combustion section 28. Other sources of cooling fluid can include, but are not limited to, fluid discharged from the LP compressor 24 or the HP compressor 26.

Figure 2:
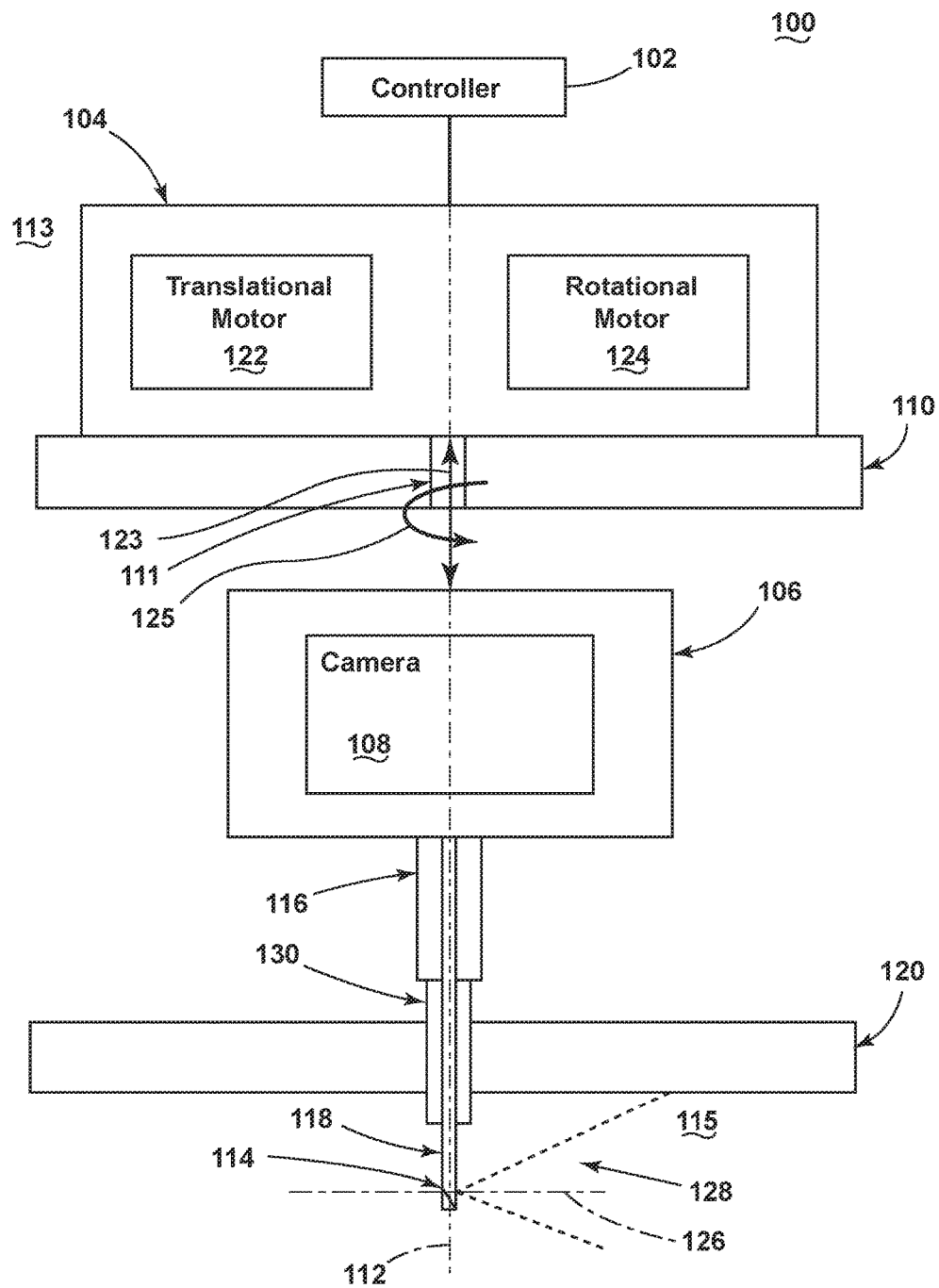
FIG. 2 is a block diagram illustrating an optical imaging system in accordance with various aspects described herein.

FIG. 2 illustrates more clearly that the core casing 46 (shown in FIG. 1) can include a radial wall 110 that defines an exterior 113 and the interior 115 of the engine 10. At least one aperture 111 can be formed in a portion of the radial wall 110 and is preferably located in proximity to a set of turbine blades 68, 70 (shown in FIG. 1) located in the interior 115 of the engine that are configured to rotate about a rotor. The rotor can be any rotary part of the engine including, but not limited, to the HP spool 48 (shown in FIG. 1) and the LP spool (shown in FIG. 1). The optical imaging system 100 is configured to image at least a portion of the interior 115 of the gas turbine engine 10 while the engine 10 is operating.

Embodiments of the optical imaging system 100 can include a housing 106, a camera 108 located within the housing 106 and an optical sight tube 118. The optical sight tube 118 extends from the housing 108 and can fixedly hold an image receiving device 114. The optical imaging system 100 can include at least one mechanism 104 that is configured to maneuver the optical sight tube 118 within the interior 115 of the gas turbine engine. The housing 106 is included and configured for mounting to the radial wall 110 of the turbine engine. The optical imaging system 100 can be manipulated to directionally control the image receiving device 114, including when inside the gas turbine engine 10.

The optical imaging system 100 can include at least one mechanism 104 that can be coupled with the housing 106 and configured to urge the optical sight tube 118 to move along or traverse 123 the longitudinal axis 112 through the aperture 111 into the interior 115 of the gas turbine engine. Further, the urging mechanism 104 can be configured to rotate the optical sight tube 118 about the longitudinal axis 112 to induce yaw 125. The urging mechanism 104 can include one or more motors useful for rotating and translating a shaft. For example, as shown, the urging mechanism 104 can include both a translational motor 122 and a rotational motor 124. The urging mechanism 104 can be formed from any device useful for urging or maneuvering the optical sight tube 118 along the longitudinal axis 112 into a cavity in the interior 115 of the turbine engine including, but not limited to, one or more permanent magnet stepper motors, hybrid synchronous stepper motors, variable reluctance stepper motors, lavet type stepping motors, AC motors, DC motors, gearboxes, etc. and combinations thereof.

Directional control of the image receiving device 114 is provided by a controller 102 external to the gas turbine engine 10. Thus, the image receiving device 114 is directionally controlled such that a selected one or more components internal to the gas turbine engine 10 can be viewed externally of the gas turbine engine 10. Parts of the optical imaging system 100 can be cooled including, but not limited to, by flowing a cooling medium along a substantial portion of the length of the optical sight tube 118 and particularly about the image receiving device 114.

As shown in FIG. 2 the housing 106 indirectly mounts to the radial wall 110 via a coupling along the longitudinal axis 112 to the urging mechanism 104. That is, the urging mechanism 104 directly mounts to the radial wall 110 at the exterior 113 of the turbine engine and the housing 106 is coupled to the urging mechanism through the aperture 111 via a shaft that can traverse 123 and yaw 125 along the longitudinal axis 112. The housing 106 can be mounted to the radial wall 110 through any known mounting method and can include direct mounting to the radial wall 110 and indirect mounting whereby the housing 106 is coupled to additional components that are mounted to the radial wall 110. The housing 106 can be made of any material suitable for protecting the housed camera 108 from high temperatures and pressures associated with gas turbine engines including, but not limited to, stainless steel, aluminum, titanium, etc.

Contained within the housing 106, the camera 108 is responsive to imaging data of one or more components of a turbine engine positioned within a field of view 128 of the image receiving device 114. The camera 108 is configured to sense a temperature of a surface in the cavity or interior 115 of the turbine engine The camera 108 can be any device for recording image data correlated to surface temperatures including, but not limited to, an infrared camera, a visible camera, a pyrometer, a multi-spectral camera, a hyperspectral camera, a charge-coupled device, an active pixel sensor, a complementary metal-oxide-semiconductor (CMOS) sensor, etc.

The optical sight tube 118 is configured to optically communicate with an interior 115 of a gas turbine engine via a distal end disposed at the interior 115 and a proximal end disposed exterior 113 of the internal turbine components. Portions of the optical sight tube 118 can be within one or more of guide tubes 116, 130. The optical sight tube 118, which can also be referred to as a borescope, extends from the housing 106 along the longitudinal axis 112 normal to the radial wall 110 towards the interior 115 of the turbine engine. The optical sight tube 118 provides a conduit of optical communication from the image receiving device 114 at the end of the optical sight tube 118 to the camera 108 within the housing 106. The optical sight tube 118 can include any components used in the transmission of optical data including, but not limited to, free space, one or more lenses, fiber optic cable and combinations thereof.

The image receiving device 114 located at the distal end of the optical sight tube 118 redirects incoming optical data to relay along the longitudinal axis 112. As shown in FIG. 2 the image receiving device relays imagery from a field of view 128 along an axis 126 normal to the longitudinal axis to enable the camera 108 to view an image substantially normal to the longitudinal axis 112. The image receiving device 114 can be configured to relay imagery from any suitable field of view 128 and axis for transmission along the longitudinal axis 112 to the camera 108. The image receiving device 114 can include any optical element known for redirecting optical imagery including but not limited to a mirror, a fiber optic, lenses and combinations thereof.

Concentric to the optical sight tube 118, one or more guide tubes 116, 130 can protect and assist to maneuver the optical sight tube 118. A moving guide tube 116 can traverse and rotate with the camera housing 106 along the longitudinal axis 112. A fixed or stationary guide tube 130 can be fixed to a wall of the turbine engine where the wall can be any interior structure within the turbine engine including, but not limited to, a radial wall that forms the vanes of a turbine stage.

When the optical sight tube 118 or borescope is maneuvered to a desired location and yaw angle, the probe optics enable the camera 108 to image the surface of the shroud 120. Advantageously, the camera 108 attached to the traversing and yawing urging mechanism 104 and coupled to the optical sight tube 118 allows the shroud 120 to be imaged while the gas turbine engine is operating. The optical sight tube along with the guide tubes 116, 130 can include multiple tubes and conduits with optical elements and passages for cooling and purging of air as will be further described below.

Measuring surface temperatures of the hot gas path components within a gas turbine engine using optical techniques requires in-situ cleaning of optical components like lenses that will get fouled from exposure to the hot gases in the gas turbine environment. Hence, the distal portion of the optical sight tube 218, which may include lenses, mirrors or combinations thereof, needs to be purged by clean air or gas. Also, in some cases, the lenses are coated with anti-reflection (AR) coatings and the AR coatings can have structural or operational temperature limits that can be less than the temperature of the hot gas path environment within the gas turbine engine. Consequently, the lenses can be cooled to avoid damage to the AR coatings. One or more inlet nozzles 236 can inject clean air or gas can into the optical sight tube 217.

Figure 3A:
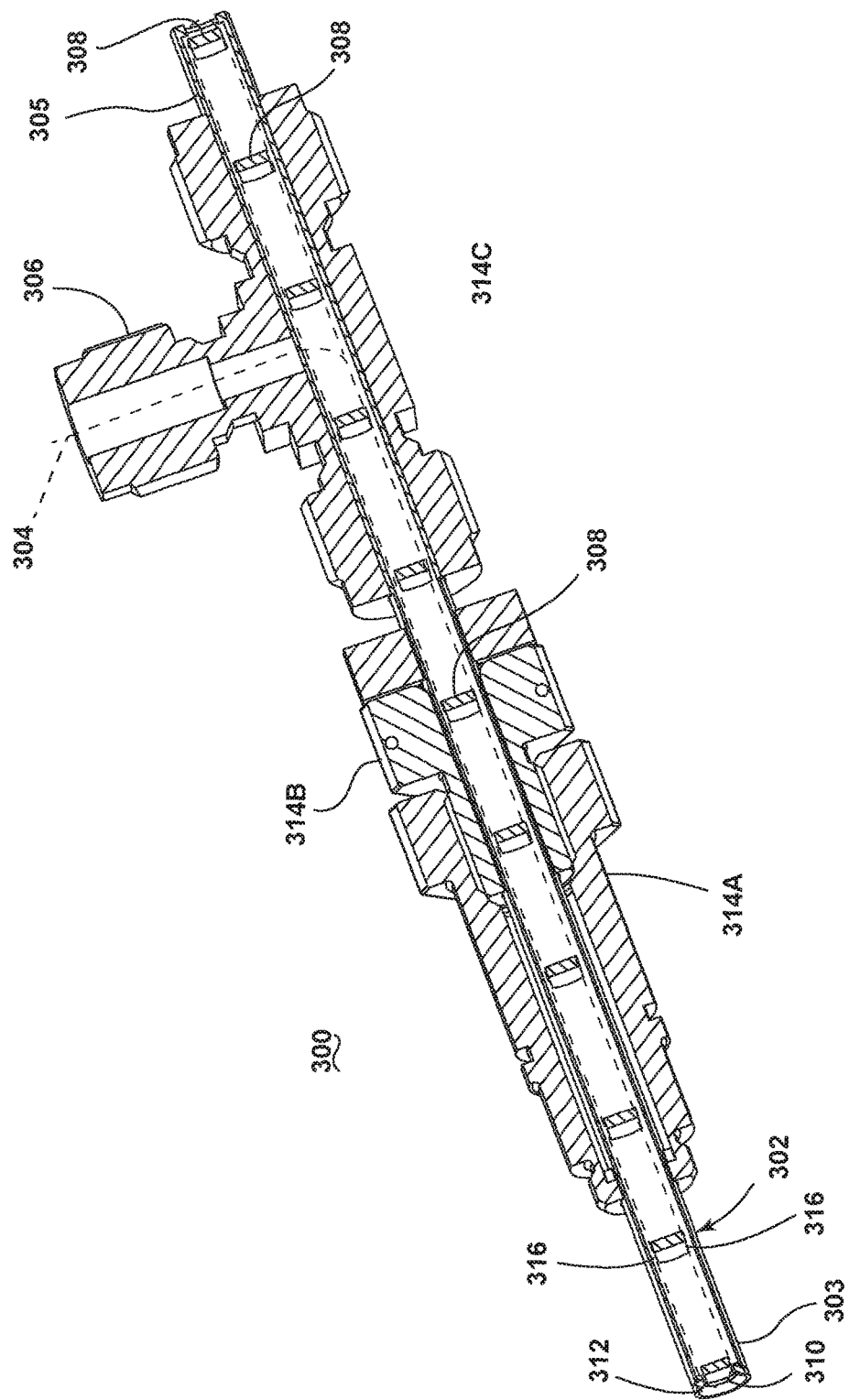
FIG. 3A is a sectional view illustrating an apparatus of an optical imaging system with an optical sight tube in accordance with various aspects described herein.
Figure 3B:
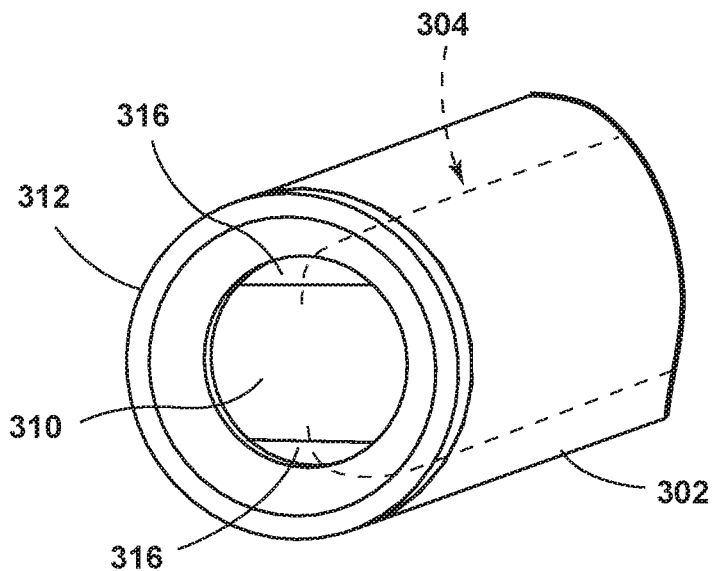
FIG. 3B is a perspective view of the distal end of the optical sight tube of FIG. 3A.
Figure 3C:
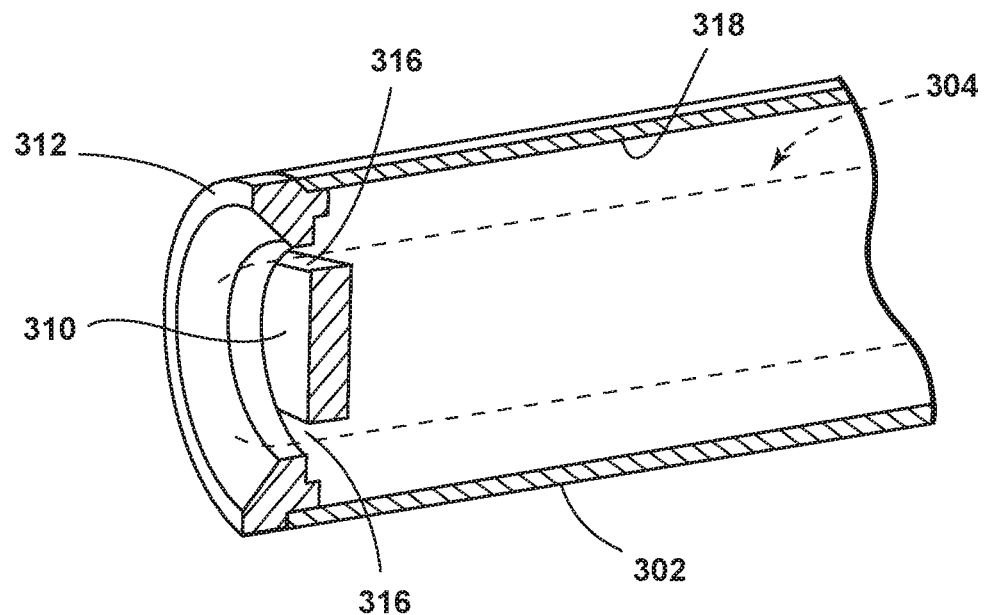
FIG. 3C is a sectional view of the distal end of the optical sight tube of FIG. 3A.

Referring now to FIG. 3A, a sectional view of an apparatus 300 for insertion through an opening in an outer casing of a gas turbine engine is shown. The apparatus 300 includes an optical sight tube 302 of which a distal end 303 is disposed at the interior of the internal turbine components and a proximal end 305 is disposed exterior of the internal turbine components. The optical sight tube 302 is defined by a longitudinal wall 318 that extends the length of the optical sight tube 302. The longitudinal wall 318 can formed in any geometrical shape useful for forming an optical sight tube, including, but not limited to an elongated cylinder. The apparatus 300 includes at least one lens 310 at the distal end 303 of the optical sight tube 302, though additional lenses 308 can be located in spaced arrangement across the extent of the optical sight tube 302.

At least one longitudinal cooling groove 316 in the longitudinal wall 318 enables the flowing of a cooling medium 304 from a location external to the turbine to cool the optical sight tube 302 at a location adjacent the distal end 303 of the optical sight tube 302. That is, one or more inlet nozzles 306 supply a cooling medium 304 such as air to the optical sight tube 302. As shown in FIGS. 3A, B and C, the lenses 308, 310 do not fully contact the longitudinal wall 318 and therefore the lenses 308, 310 include grooves that correspond with the longitudinal cooling grooves 316 in the longitudinal wall 318 of the optical sight tube 302. The cooling medium 304 flows along the extent of optical sight tube 302 along one or more longitudinal cooling grooves 316 in the longitudinal wall 318 and purges at the distal end 303 of the optical sight tube 302 through one or more openings between an end component 312 of the optical sight tube 302 and the distal lens 310.

One or more guide tubes 314A, B, and C can be in concentric alignment with portions of the optical sight tube 302. The outer guide tube 314A terminates short of the distal end 303 of the optical sight tube 302. Hence, for applications where a small diameter borehole exists at the hot gas path, the apparatus 300 permits an optical imaging system to inspect internal turbine components at elevated temperatures.

Figure 4A:
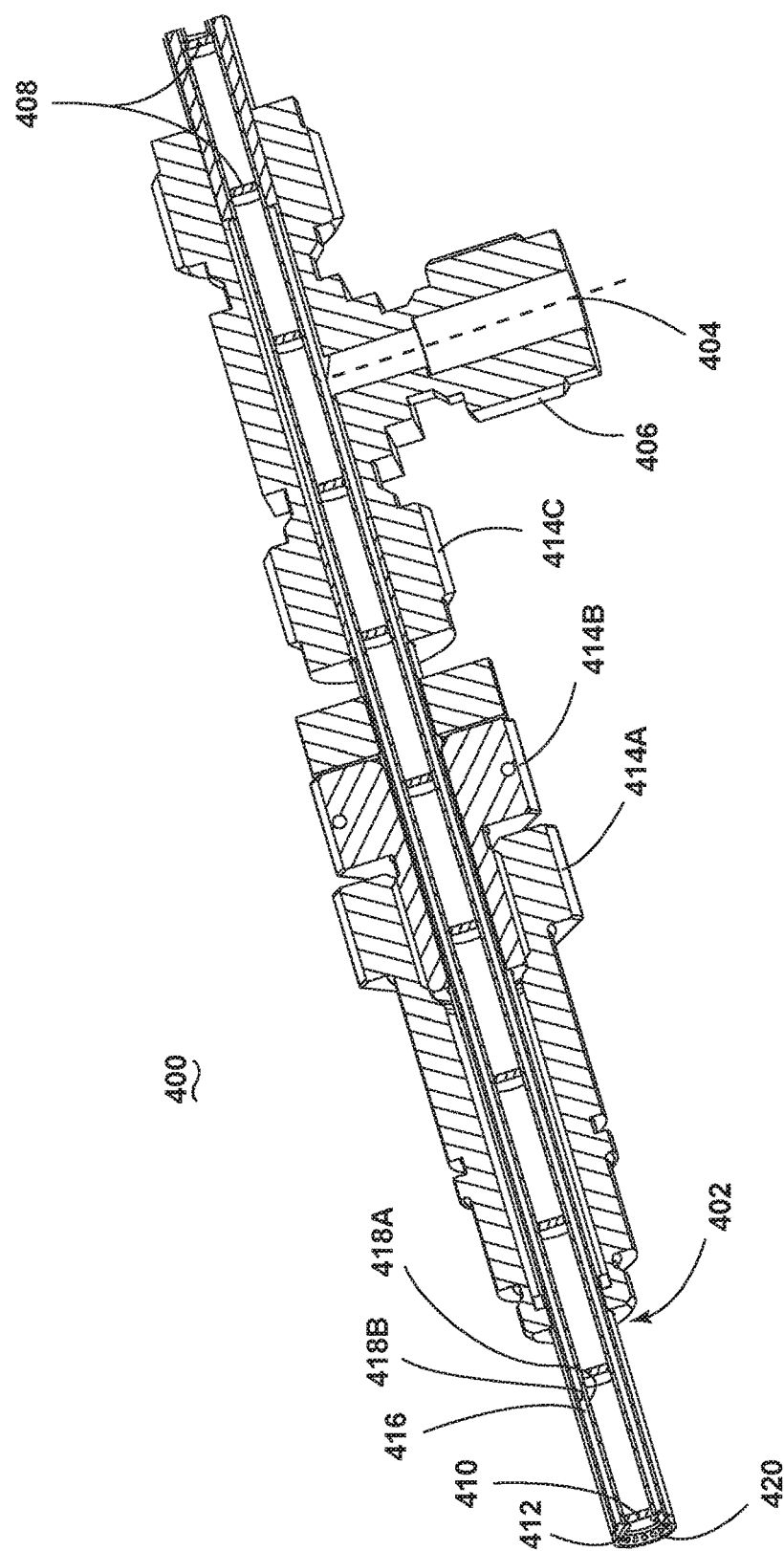
FIG. 4A is a sectional view illustrating apparatus of an optical imaging system with an optical sight tube in accordance with various aspects described herein.
Figure 4B:
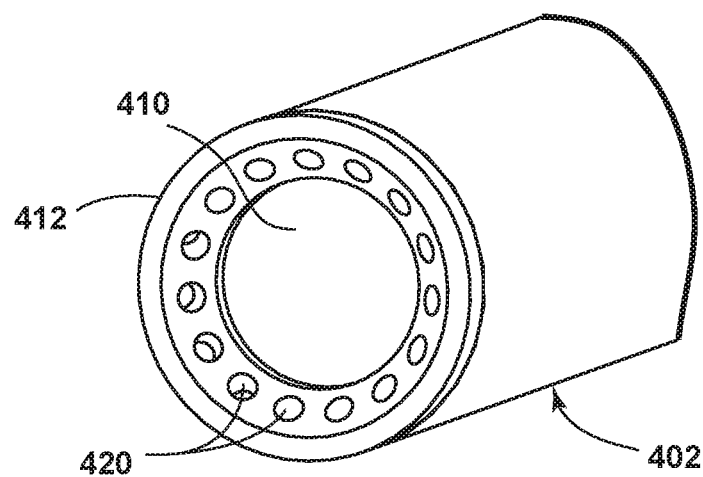
FIG. 4B is a perspective view of the distal end of the optical sight tube of FIG. 4A.
Figure 4C:
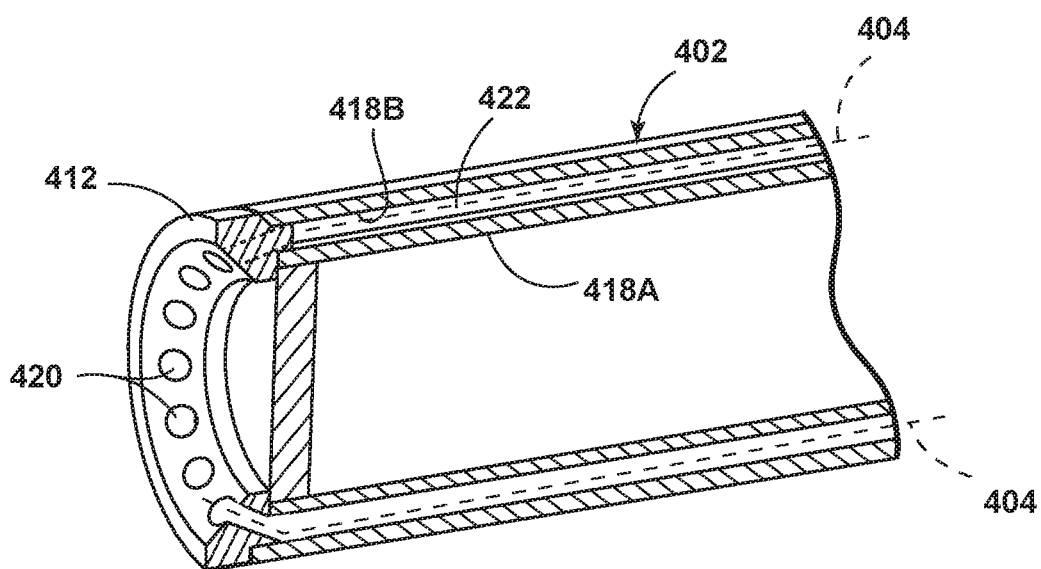
FIG. 4C is a sectional view of the distal end of the optical sight tube of FIG. 4A.

FIG. 4A is a sectional view illustrating an apparatus 400 of an optical imaging system with an optical sight tube 402 in accordance with various aspects described herein. The apparatus 400 is similar to that illustrated in FIG. 3A; therefore, like parts will be identified with like numerals increased by 100, with it being understood that the description of the like parts of the first apparatus applies to the second apparatus, unless otherwise noted.

The optical sight tube 402 includes two concentric longitudinal walls; an inner longitudinal wall 418A and an outer longitudinal wall 418B in spaced relation to one another. The cavity between the inner longitudinal wall 418A and the outer longitudinal wall 418B defines a longitudinal cooling groove 416. The longitudinal cooling groove 416 directs the cooling medium 404 from the inlet nozzle 406 connected to an external source to a plurality of holes 420 in the longitudinal wall 418A adjacent the distal lens 410. The cooling medium 404 flows from the plurality of holes toward the distal lens 410.

Figure 5A:
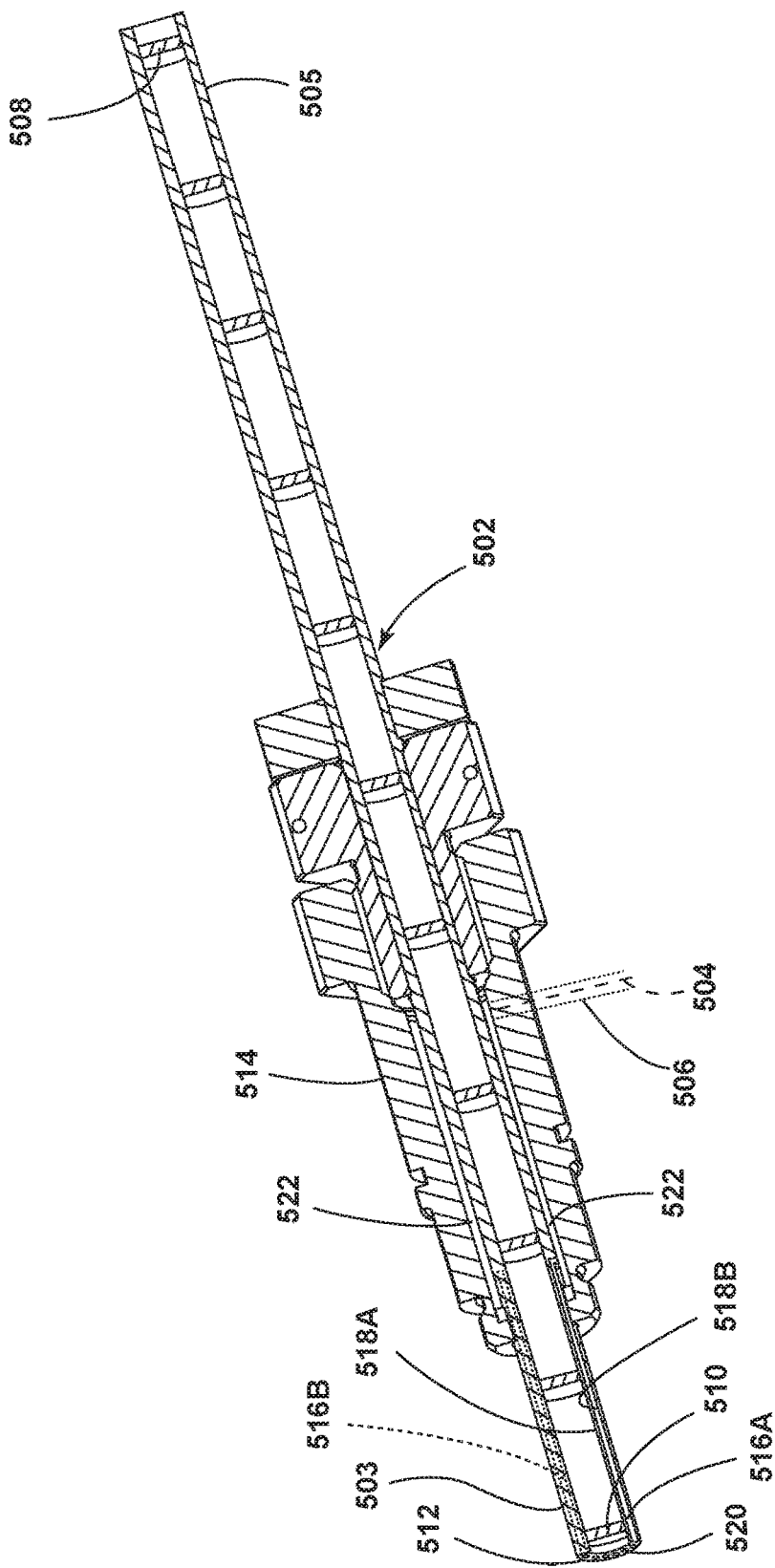
FIG. 5A is a sectional view illustrating another apparatus of an optical imaging system with an optical sight tube in accordance with various aspects described herein.
Figure 5B:
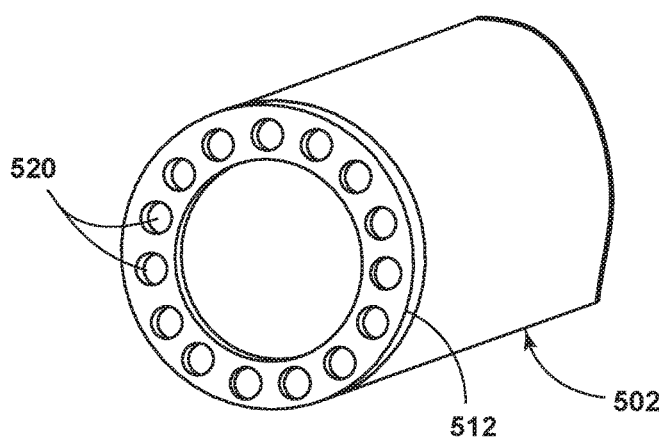
FIG. 5B is a perspective view of the distal end of the optical sight tube of FIG. 5A.
Figure 5C:
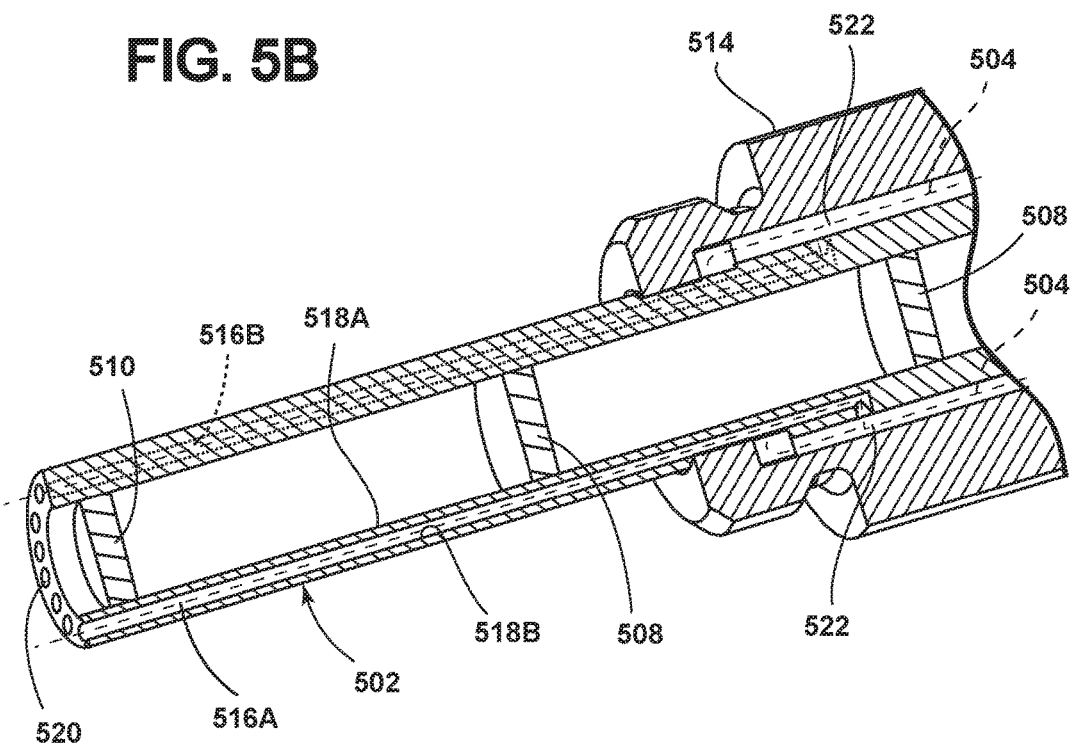
FIG. 5C is a sectional view of the distal end of the optical sight tube of FIG. 5A.

FIG. 5A is a sectional view illustrating another apparatus 500 of an optical imaging system with an optical sight tube 502 in accordance with various aspects described herein. The apparatus 500 is similar to that illustrated in FIG. 4A; therefore, like parts will be identified with like numerals increased by 100, with it being understood that the description of the like parts of the first apparatus applies to the second apparatus, unless otherwise noted.

The cooling medium 504 enters the guide tube 514 nearest the distal end 503 of the optical sight tube 502. The cooling medium 504 flows through one or more cooling grooves 522 within the guide tube 514. The optical sight tube 502 includes a plurality of longitudinal cooling grooves 516A and B that overlie a portion of the cooling grooves 522 within the guide tube 514. The cooling medium 504 flows from the cooling grooves 522 through the longitudinal cooling grooves 516A and B. The cooling medium 504 is purged through the plurality of holes 520 at the end component 512 of the longitudinal wall 518A. The plurality of holes 520 adjacent to the distal end 503 of the optical sight tube 502 direct the cooling medium 504 from the longitudinal grooves 516A and B towards the lens 510 at the distal end 503 of the optical sight tube 502 to purge the lens 510.

There can be any number of holes 520 and longitudinal grooves 516 useful for purging air adjacent the distal end 503 of the optical sight tube 502 including, but not limited to, a configuration where there is a one-to-one relationship between the plurality of holes 520 and the plurality of longitudinal grooves 516 or where there is a many-to-one relationship between the plurality of holes 520 and the plurality of longitudinal grooves 516.

Additionally, the plurality of holes 420, 520 in the longitudinal wall 418, 518 adjacent the lens 410, 510 at the distal end 403, 503 of the optical sight tube 402, 502 can include any configuration useful for directing air to purge and cool the lens 410, 510 including, but not limited to, directing cooling medium 504 in a direction substantially perpendicular to the lens 510 at the distal end 503 of the optical sight tube 504, directing cooling medium across the lens 510 at the distal end 503 of the optical sight tube 504 and combinations thereof.

Benefits of the above-described embodiments include an optical imaging system that does not include positioning a guide tube near the front end of the optics system. The resulting optical imaging system is constrained only by the diameter of the optical sight tube as opposed to the larger diameter guide tube. Hence, for cases where small diameter boreholes exist at the hot gas path, an optical image system implementing the above-described apparatus for insertion through an opening in an outer casing of a gas turbine engine can be used.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for insertion through an opening in an outer casing of a turbine engine and inspection of internal turbine components at elevated temperatures comprising:
    a hollow optical sight tube configured to optically communicate with an interior of a gas turbine engine via a distal end disposed at the interior of the gas turbine engine and a proximal end disposed exterior of the internal turbine components and defined by a first longitudinal wall defining a continuous, even, and concentric interior surface; and
    at least two lenses received within the hollow optical sight tube, the at least two lenses fixed to a first portion of the interior surface of the first longitudinal wall at the distal end of the optical sight tube, and not fully contacting a second portion of the longitudinal wall, wherein a space between the second portion and the at least two lenses defines a longitudinal lens cooling groove of each of the at least two lenses, and wherein the cooling groove of each of the at least two lenses are axially aligned along the first longitudinal wall, the lens cooling groove arranged for flowing a cooling medium from a location external to the turbine to cool the hollow optical sight tube at a location at least adjacent the distal end.

2. The apparatus of claim 1 further comprising a plurality of holes in the longitudinal wall, the plurality of holes adjacent the lens to direct cooling medium from the respective groove toward the lens to purge the lens.

3. The apparatus of claim 1 comprising a plurality of longitudinal cooling grooves.

4. The apparatus of claim 1 further including an inlet nozzle removably secured to the optical sight tube to supply the cooling medium.

5. The apparatus of claim 1 further including a plurality of lenses located in spaced arrangement across the extent of the optical sight tube.

6. The apparatus of claim 1 wherein the distal end of the optical sight tube defines a radial aperture receiving of the at least two lenses, and wherein the respective lens cooling groove is defined by a portion of the radial aperture between the lens and the distal end.

7. The apparatus of claim 1 wherein the optical sight tube is an elongated cylinder.

8. The apparatus of claim 7 wherein the optical sight tube is hollow except for the at least two lenses.

9. The apparatus of claim 1 wherein the at least two lenses are received at an axial location, and wherein the first portion and the second portion of the first longitudinal wall are axially aligned with the axial location.

10. An optical sight tube for viewing internal components of a turbine engine, comprising:
    a first elongated wall defining a continuous, even, and concentric interior surface; and
    at least two lenses proximate to an interior distal end of the first elongated wall, each of the at least two lenses fixed at a relative first portion of the interior surface of the first elongated wall and not fully contacting a relative second portion of the interior surface of the first elongated wall, wherein a space between the second portion and the at least two lenses defines a lens cooling groove of each of the at least two lenses, and wherein the cooling groove of each of the at least two lenses are axially aligned along the first elongated wall such that the lens cooling groove is configured for flowing a cooling medium from a location external to the turbine to cool the optical sight tube at a location at least adjacent the distal end.

11. The optical sight tube of claim 10 comprising a plurality of longitudinal cooling grooves.

12. The optical sight tube of claim 10 further including a connection for removably securing an inlet nozzle to supply the cooling medium.

13. The optical sight tube of claim 10 further including a plurality of lenses located in spaced arrangement across the extent of the optical sight tube.

14. The apparatus of claim 10 wherein the optical sight tube is an elongated cylinder.

15. The apparatus of claim 10 wherein the optical sight tube is hollow except for the at least two lenses.

16. The apparatus of claim 10 wherein the at least two lenses is received at an axial location of the first elongated wall, and wherein the first portion and the second portion of the first elongated wall are axially aligned with the axial location.

* * * * *

UNITED STATES PATENT AND TRADEMARK OFFICE
CERTIFICATE OF CORRECTION

PATENT NO.        : 10,473,528 B2
APPLICATION NO.   : 15/043508
DATED             : November 12, 2019
INVENTOR(S)       : Mohamed Sakami, Nirm Nirmalan and Jeremy Bailey Page 1 of 1

It is certified that error appears in the above-identified patent and that said Letters Patent is hereby corrected as shown below:

Column 8 Claim 6, Line 2, after "receiving" insert --one--.

Signed and Sealed this
Sixteenth Day of June, 2020

Andrei Iancu
*Director of the United States Patent and Trademark Office*